United States Patent [19]
Takahashi et al.

[11] Patent Number: 5,703,267
[45] Date of Patent: Dec. 30, 1997

[54] PROCESS FOR PRODUCING 2-CYANOACRYLIC ACID

[75] Inventors: Shin Takahashi; Yoshiharu Ohashi; Yushi Ando; Toshio Okuyama, all of Nagoya, Japan

[73] Assignee: Toagosei Co., Ltd., Tokyo, Japan

[21] Appl. No.: 621,612

[22] Filed: Mar. 26, 1996

[30] Foreign Application Priority Data

Mar. 27, 1995 [JP] Japan ................... 7-092969

[51] Int. Cl.$^6$ .................................. C07C 255/03
[52] U.S. Cl. ........................................ 558/451
[58] Field of Search ............................. 558/451

[56] References Cited

U.S. PATENT DOCUMENTS 3,444,233  5/1969  Rabinowitz ............................ 260/465

Primary Examiner—Jose G. Dees
Assistant Examiner—Ebenezer Sackey
Attorney, Agent, or Firm—Browdy and Neimark

[57] ABSTRACT

The present invention provides a process for producing 2-cyanoacrylic acid, characterized by subjecting a 2-cyanoacrylate and an organic acid to transesterification reaction. The 2-cyanoacrylic acid obtained by the process of the present invention is useful as a starting material for the preparation of polyfunctional 2-cyanoacrylates.

15 Claims, 1 Drawing Sheet

PROCESS FOR PRODUCING 2-CYANOACRYLIC ACID

BACKGROUND OF THE INVENTION

1. Field of the Invention

The present invention relates to a process for producing 2-cyanoacrylic acid useful as a starting material for the preparation of 2-cyanoacrylates widely used as a main component of cyanoacrylate adhesives, particularly, polyfunctional 2-cyanoacrylates which have been considered to be difficult to produce.

2. Related Art Statement

Cyanoacrylate adhesives mainly composed of a 2-cyanoacrylate have the property that the 2-cyanoacrylate as the main component easily anionically polymerizes in the presence of a slight amount of water and a basic substance to result in rapid setting. Therefore, they are widely used as instantaneous adhesives in various industrial fields, in the medical fields, in the leisure fields and, besides, in the household.

The conventional cyanoacrylate instantaneous adhesives are high in tensile bond strength at room temperature, but not necessarily high in peel bond strength or impact bond strength. Moreover, higher heat resistance and water resistance are demanded and further improvements thereof are desired.

The conventional cyanoacrylate instantaneous adhesives utilize the polymers obtained by anionic polymerization of 2-cyanoacrylates for bonding. It is presumed that the above insufficient properties are caused because the polymers obtained by anionic polymerization are linear high polymers having no crosslinked structure.

As a method for solving these defects, it has been reported to add acidic substances, various polyacrylate esters, rubbers, modified polymers, etc. However, since these do not copolymerize with 2-cyanoacrylates, it is difficult to attain substantial improvement of the properties.

Under the circumstances, it has been reported that polyfunctional 2-cyanoacrylates copolymerizable with 2-cyanoacrylates are added to the 2-cyanoacrylates and copolymerized with the 2-cyanoacrylates, thereby to provide a crosslinked structure for the 2-cyanoacrylate polymers to improve the properties thereof.

However, it is difficult to prepare these polyfunctional compounds by the process employed at present for industrial preparation of 2-cyanoacrylates, namely, the process which comprises condensing formaldehyde with cyanoacetates and depolymerizing the condensates.

In the past, therefore, a process which utilizes the Diels-Alder reactions of anthrathene or cyclopentadiene with 2-cyanoacrylates was employed for the production of the polyfunctional compounds. However, the reactivity in these reactions is low and separation of the products is not easy. Thus, the process is industrially unsuitable.

On the other hand, if 2-cyanoacrylic acid can be utilized for the preparation of these polyfunctional compounds, it is supposed that various 2-cyanoacrylates can easily be obtained by the esterification reaction of 2-cyanoacrylic acid with alcohols or by preparing 2-cyanoacrylic acid chloride from 2-cyanoacrylic acid and reacting the resulting 2-cyanoacrylic acid chloride with alcohols as in the usual process for the preparation of acrylate esters.

However, only the process for the production of 2-cyanoacrylic acid by pyrolysis of 2-cyanoacrylates disclosed in German Patent Application Laid-Open No.3415181 has been reported as a technique of producing 2-cyanoacrylic acid. This is probably because it has been considered as impossible to treat 2-cyanoacrylates at suitable temperatures since 2-cyanoacrylates have the characteristic that they readily anionically polymerize even at room temperature in the presence of a slight amount of water or a basic substance.

The above process comprises pyrolyzing 2-cyanoacrylates at high temperatures of 350°–800° C. and is difficult to industrialize. In addition, since the pyrolysis temperature is much higher than 130° C. which is the decomposition temperature of the target 2-cyanoacrylic acid, there is great possibility of the resulting 2-cyanoacrylic acid being decomposed, and no high yield can be expected.

OBJECT OF THE INVENTION

The inventors have conducted research on a process by which 2-cyanoacrylic acid can be produced at low temperatures at which 2-cyanoacrylic acid does not undergo pyrolysis, and a process by which 2-cyanoacrylic acid can be obtained at a high conversion, and, particularly, a process by which 2-cyanoacrylic acid can be industrially produced.

SUMMARY OF THE INVENTION

They have found that 2-cyanoacrylic acid can be obtained at a high conversion even at low reaction temperatures by subjecting a 2-cyanoacrylate to an acid transesterification reaction, i.e. an acidolysis using an organic acid. Thus, the present invention has been accomplished.

That is, the present invention relates to a process for producing 2-cyanoacrylic acid by the acidolysis reaction of a 2-cyanoacrylate using an organic acid.

DETAILED DESCRIPTION OF THE INVENTION

Figure 1:
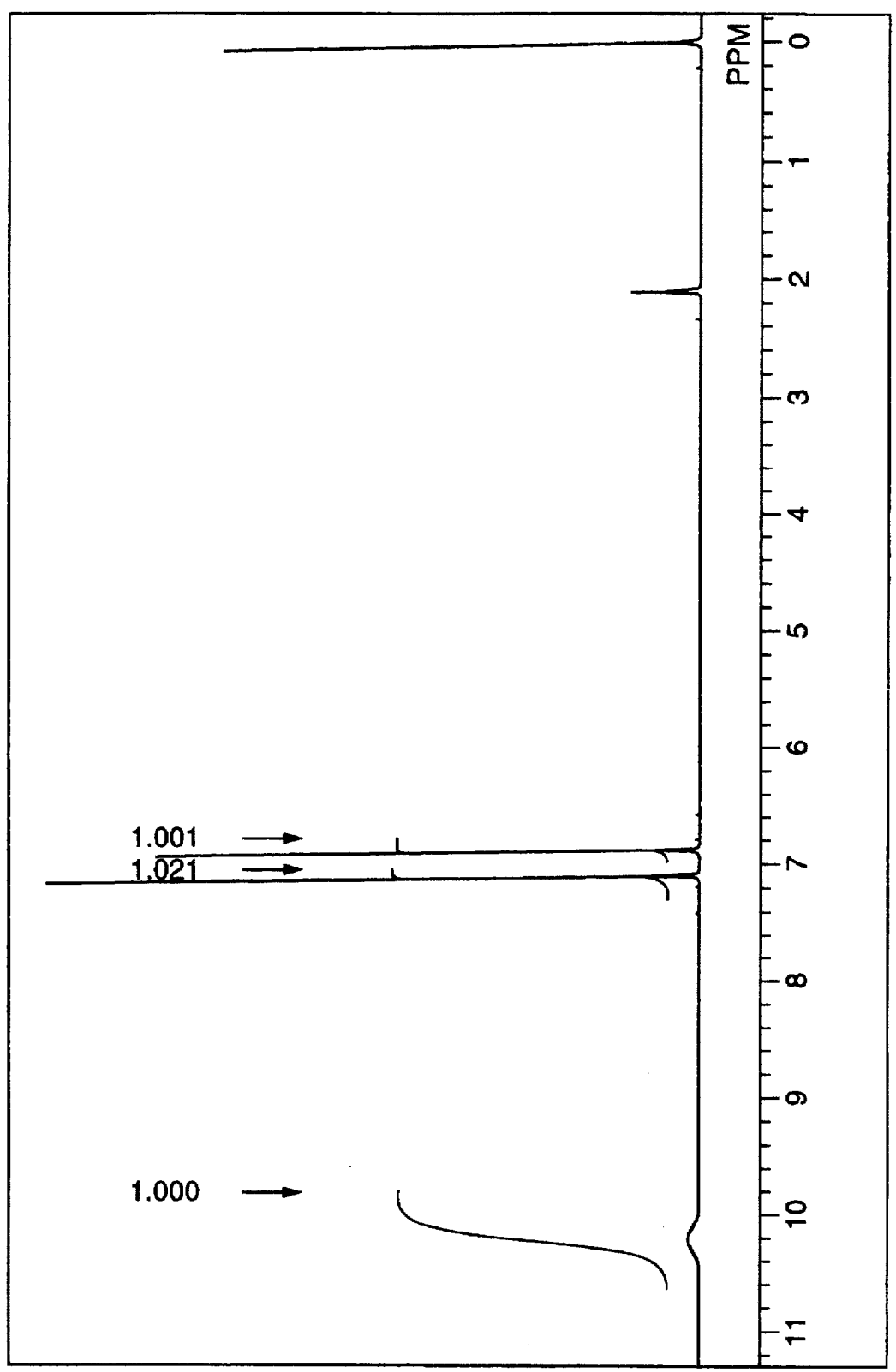
FIG. 1 is a proton NMR chart of 2-cyanoacrylic acid obtained in Example 1.

The process for the production of 2-cyanoacrylic acid according to the present invention will be explained in detail below.

The 2-cyanoacrylates used as a starting material in the present invention include various 2-cyanoacrylates widely used as a main component of cyano acrylate adhesives. Examples thereof are enumerated below, but these are not limitative and other various 2-cyanoacrylates can be used in the present invention.

That is, they are methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxyethyl, methoxybutyl, ethoxyethyl, propoxyethyl, butoxymethyl and butoxyethyl esters of 2-cyanoacrylic acid. These are all used as main components of cyanoacrylate instantaneous adhesives.

Especially preferred are methyl-2-cyanoacrylate, ethyl-2-cyanoacrylate, isopropyl-2-cyanoacrylate, n-propyl-2-cyanoacrylate, n-butyl-2-cyanoacrylate, and isobutyl-2-cyanoacrylate, because when these are used, the organic acid esters by-produced by the acid transesterification can be distilled off at low temperatures.

As the organic acids used in the present invention, mention may be made of aromatic compounds such as benzoic acid and phthalic acid, but more preferred are fatty acids. Various fatty acids can be referred to and examples thereof are formic acid, acetic acid, propionic acid, butyric acid, isobutyric acid, valeric acid, trimethylacetic acid, caproic acid, n-hexanoic acid, 2-methyl-pentanoic acid, n-octanoic acid, n-decanoic acid, lauric acid, palmitic acid, stearic acid, oleic acid, fluoroacetic acid, chloroacetic acid, bromoacetic acid, iodoacetic acid, dichloroacetic acid, trichloroacetic acid, chloropropionic acid, acrylic acid, methacrylic acid, cyanoacetic acid and vinylacetic acid. Various other organic acids can also be used.

Especially preferable organic acids in the present invention are formic acid, acetic acid, propionic acid and butyric acid, because when these organic acids are used, unreacted organic acids after the acid transesterification reaction and by-produced organic acid esters can be easily distilled off and there is no fear of occurrence of polymerization. The most preferable organic acid is acetic acid.

The molar ratio of the 2-cyanoacrylate and the organic acid in the acid transesterification reaction is unlimited, but it is preferred to use the organic acid in an excess amount in order to give to the organic acid the function as a reaction solvent as explained hereinafter. Thus, the molar ratio of organic acid/2-cyanoacrylate is preferably 100-1, more preferably 50-2.

As the reaction catalysts used for the acid transesterification reaction in the present invention, mention may be made of Lewis acids, acid catalysts, etc. which are known as catalysts for transesterification reaction, but cation exchange resins are preferred in the present invention.

The cation exchange resin as the catalyst is used in such a manner that it is packed in a column and a mixture of the organic acid and the 2-cyanoacrylate is passed through the column to react them. More simply, the 2-cyanoacrylate, a fatty acid and the cation exchange resin are charged in a reaction vessel and they are allowed to react under stirring.

The amount of the cation exchange resin in carrying out the reaction in a reaction vessel is adjusted to such an amount that the reaction mixture can be stirred and the reaction can proceed efficiently. The amount of the cation exchange resin is generally 1–80% by weight, preferably 20–70% by weight based on the total weight of the 2-cyanoacrylate, the organic acid and the cation exchange resin.

The acid transesterification reaction of the present invention proceeds in a wide temperature range, but the reaction temperature is preferably 10°–130° C. in the present invention for the following reasons.

If the reaction temperature is lower than 10° C., the reaction rate is slow and, furthermore, industrial utility value is low. If it is higher than 130° C., pyrolysis of 2-cyanoacrylic acid and polymerization of the starting 2-cyanoacrylate occur to cause decrease in the conversion to 2-cyanoacrylic acid. More preferable reaction temperature is 40°–90° C.

In the acid transesterification reaction of the present invention, the organic acid used in excess of the reacting amount can be used as a reaction medium. Furthermore, as a process preferable for preventing anionic polymerization of 2-cyanoacrylate, a solvent can be separately added as a reaction medium, and known solvents, for example, organic solvents such as toluene can be utilized as the reaction medium.

For the acid transesterification reaction of the present invention, hydroquinone, hydroquinone monomethyl ether, etc. can be used as radical polymerization inhibitors, and sulfur dioxide, $BF_3$, p-toluenesulfonic acid, phosphorus pentoxide, polyphosphoric acid, etc. can be used as anionic polymerization inhibitors.

The acid transesterification reaction of the present invention need not be carried out at such high temperatures as of 350°–800° C. reported in the conventional techniques, and loss of the target 2-cyanoacrylic acid can be considerably reduced. In addition, the conversion is high and this has industrially practical value.

According to the present invention, industrialization of the production of 2-cyanoacrylic acid becomes possible, and, at the same time, industrialization of the production of various 2-cyanoacrylates using the resulting 2-cyanoacrylic acid also becomes possible. As a result, improved cyanoacrylate adhesives can be provided, and, therefore, the present invention makes a great contribution in various industrial fields, in medical fields, in leisure fields, in the fields of general household and stationery materials for school children, etc.

DESCRIPTION OF PREFERRED EMBODIMENTS

The following Examples are intended to explain the present invention in more detail and are not intended to limit the scope of the invention in any manner.

Example 1

25 parts by weight of purified ethyl-2-cyanoacrylate, 144 parts by weight of acetic acid and 200 parts by weight of a cation exchange resin (Amberlist 15) were charged together with 2 parts by weight of p-toluenesulfonic acid and 2 parts by weight of hydroquinone in a reaction vessel and a reaction was carried out at 80° C. for 20 hours with stirring.

A proton NMR analysis of the reaction mixture showed that 2-cyanoacrylic acid was produced at a conversion of 25% in view of the amount of ethyl acetate produced.

Unreacted acetic acid and ethyl-2-cyanoacrylate were distilled off at 70° C. under 5 mmHg or lower, and then concentrated residue was recrystallized from toluene to give pure material. The resulting white powder was subjected to a proton NMR analysis (solvent: acetone $D_6$) to find that doublets belonging to the protons of $CH_2=C$ of 2-cyanoacrylic acid appeared at 6.9 ppm and 7.1 ppm and a singlet belonging to the proton of COOH of 2-cyanoacrylic acid appeared at 10.2 ppm and the integral ratio thereof was 1:1:1. Thus, it was confirmed that the powder compound was 2-cyanoacrylic acid. The NMR chart is shown in FIG. 1.

The reaction conditions and results are summarized in Table 1.

Examples 2–12

Transesterification reactions were carried out in the same manner as in Example 1 under the conditions shown in Table 1. The results are also shown in Table 1.

It can be seen from the results that when a cation exchange resin is used as the catalyst, the acid transesterification reaction of the cyanoacrylate and the organic acid smoothly proceeds and loss caused by the polymerization reaction can be reduced. Moreover, it has become clear that the reaction rate increases with increase in the amount of the cation exchange resin and the reaction proceeds faster with rising of the reaction temperature.

However, with rising of the reaction temperature, the loss due to the polymerization reaction increases. Therefore, a suitable reaction temperature is 10°–130° C., and a more suitable reaction temperature is 40°–90° C.

TABLE 1

| | | | 1 | 2 | 3 | 4 | 5 | 6 | 7 | 8 | 9 | 10 | 11 | 12 |
|---|---|---|---|---|---|---|---|---|---|---|---|---|---|---|
| Reaction conditions | Amount of ethyl-2-cyanoacrylate | Part by weight | 25 | 25 | 25 | 25 | 25 | 25 | 25 | 25 | 25 | 25 | 25 | 25 |
| | Amount of acetic acid | Part by weight | 144 | 144 | 144 | 144 | 144 | 144 | 144 | 144 | 144 | 144 | 144 | 144 |
| | Amount of cation exchange resin | Part by weight | 200 | 200 | 200 | 300 | 300 | 300 | 300 | 300 | 300 | 300 | 100 | 200 |
| | p-Toluene-sulfonic acid | Part by weight | 2 | 2 | 2 | 2 | 2 | 2 | 2 | 2 | 2 | 2 | 2 | 2 |
| | Hydroquinone | Part by weight | 2 | 2 | 2 | 2 | 2 | 2 | 2 | 2 | 2 | 2 | 2 | 2 |
| | Reaction temperature | °C. | 80 | 90 | 100 | 40 | 50 | 60 | 70 | 60 | 60 | 60 | 60 | 60 |
| | Reaction time | hr | 20 | 20 | 20 | 120 | 120 | 120 | 120 | 12 | 48 | 96 | 120 | 120 |
| Results | Transesterification rate | % | 25 | 35 | 43 | 19 | 37 | 67 | 32 | 23 | 41 | 60 | 33 | 55 |
| | Loss due to polymerization | % | 8 | 20 | 55 | 0 | 3 | 5 | 25 | 0 | 1 | 2 | 7 | 8 |

What is claimed is:

1. A process for producing a 2-cyanoacrylic acid which comprises subjecting a 2-cyanoacrylate and an organic acid to a transesterification reaction at a temperature of 40°–90° C.

2. A process according to claim 1, wherein a cation exchange resin is used as a catalyst.

3. A process according to claim 1, wherein the organic acid is selected from the group consisting of formic acid, acetic acid, propionic acid and butyric acid.

4. A process according to claim 1, wherein the organic acid is acetic acid.

5. A process according to claim 1, wherein the 2-cyanoacrylate is selected from the group consisting of methyl-2-cyanoacrylate, ethyl-2-cyanoacrylate, isopropyl-2-cyanoacrylate, n-propyl-2-cyanoacrylate, n-butyl-2-cyanoacrylate, and isobutyl-2-cyanoacrylate.

6. A process according to claim 1, wherein the molar ratio of the organic acid/the 2-cyanoacrylate is 50-2.

7. A process according to claim 1, wherein a cation exchange resin as a catalyst is used in an amount of 20–70% by weight based on the total weight of the 2-cyanoacrylate, the organic acid and the cation exchange resin.

8. A process for producing 2-cyanoacrylic acid which comprises subjecting a 2-cyanoacrylate to an acidolysis reaction with an organic acid at a temperature of 10°–90° C.

9. A process according to claim 8, wherein a cation exchange resin is used as a catalyst.

10. A process according to claim 8, wherein the organic acid is selected from the group consisting of formic acid, acetic acid, propionic acid and butyric acid.

11. A process according to claim 8, wherein the organic acid is acetic acid.

12. A process according to claim 8, wherein the 2-cyanoacrylate is selected from the group consisting of methyl-2-cyanoacrylate, ethyl-2-cyanocacrylate, isopropyl-2-cyanoacrylate, n-propyl-2-cyanoacrylate, n-butyl-2-cyanoacrylate, and isobutyl-2-cyanoacrylate.

13. A process according to claim 8, wherein the molar ratio of the organic acid/the 2-cyanoacrylate is 50-2.

14. A process according to claim 8, wherein a cation exchange resin as a catalyst is used in an amount of 20–70% by weight based on the total weight of the 2-cyanoacrylate, the organic acid and the cation exchange resin.

15. A process according to claim 8, wherein said reaction is carried out at a temperature no greater than about 60° C.

* * * * *